United States Patent [19]
Allred, III et al.

[11] Patent Number: 4,790,294
[45] Date of Patent: Dec. 13, 1988

[54] BALL-AND-SOCKET BEAD ENDOSCOPE STEERING SECTION

[75] Inventors: Jimmie B. Allred, III, Skaneateles; Richard Bingham, Auburn, both of N.Y.

[73] Assignee: Welch Allyn, Inc., Skaneatesles Falls, N.Y.

[21] Appl. No.: 78,713

[22] Filed: Jul. 28, 1987

[51] Int. Cl.⁴ .................................................. A61B 1/00
[52] U.S. Cl. .......................................... 128/4; 138/120
[58] Field of Search ........................ 128/4, 6; 138/120

[56] References Cited

U.S. PATENT DOCUMENTS

| | | | |
|---|---|---|---|
| 3,190,286 | 6/1965 | Stokes | 128/6 |
| 3,557,780 | 1/1971 | Sato | 128/4 |
| 3,583,393 | 6/1971 | Takahashi | 128/4 |
| 3,610,231 | 10/1971 | Takahashi | 128/6 |
| 3,669,098 | 6/1972 | Takahashi | 128/6 |
| 3,739,770 | 6/1973 | Mori | 128/6 |
| 3,799,151 | 3/1974 | Fukaumi et al. | 128/6 |
| 4,347,837 | 9/1982 | Hosono | 128/6 |
| 4,700,693 | 10/1987 | Lia et al. | 128/4 |

Primary Examiner—William H. Grieb
Attorney, Agent, or Firm—Wall and Roehrig

[57] ABSTRACT

A steering section for an endoscope or borescope employs a plurality of steering cables that pass through peripheral bores of axially aligned flat washers. Pairs of beads are strung on the cables between the washers to define hinge points for the bending of the steering section. Each pair of beads include a spherical-nose ball bead and a countersunk socket bead. A through-passage in the ball bead has a relatively narrow nose portion with a small clearance with respect to the steering cable, and a tapered or countersunk portion that expands basewards and prevents the spacer bead from binding the cable. The axial bores in the washers are tapered out fore and aft from a relatively narrow waist portion so that the cable touches the washer only at a single point. Limiter beads of about half the thickness of the spacing between washers limit the bending of the steering section.

18 Claims, 1 Drawing Sheet

BALL-AND-SOCKET BEAD ENDOSCOPE STEERING SECTION

BACKGROUND OF THE INVENTION

This invention relates generally to controllably bendable tube assemblies, and is more especially directed to a hollow steering section of a borescope or endoscope.

An endoscope is generally characterized as an elongated flexible tube with a viewing head in its distal or forward end, and a control housing at its proximal end for controlling or steering the distal end. Such an endoscope has a bendable-tube steering section at the distal end adjacent to the viewing head. One or two pairs of control cables extend through the bendable-tube steering section and through the remainder of the flexible tube, and these cables connect with a steering control in the control section. One or both pairs of these cables are displaced to bend the bendable-tube steering section to facilitate the inspection of an object.

An endoscope is typically inserted into a body cavity of a patient to investigate visually the tissues within the cavity. For example, an endoscope can be inserted into the colon or stomach, or into the lung of a patient. Because the esophagus, bronchii, and the colon are narrow, tortuous passageways, the steering section must be bent rather precisely, and as close to the head as possible, in order to obtain the necessary penetration without damaging the patient's tissues. It is most desireable that the play or slack in the cable be kept to an absolute minimum, so that steering can be controlled precisely.

A borescope is a similar device, but intended for visual inspection of a mechanical device, such as a jet engine or turbine, where it would be difficult or impossible to examine the device's internal elements. The borescope needs to go into narrow tortuous passageways, and must observe similar steering and bending considerations.

A number of types of steering mechanisms are known. For example, helically coiled strips are employed in endoscopes or borescopes as described in U.S. Pat. Nos. 3,610,231 and 3,739,770. Steering sections having thin-walled cylindrical segments or bands that are joined by means of pins or bifurcations or other similar articulations such that the segments are rockable on one another, are described in U.S. Pat. Nos. 3,583,393; 3,669,098; 3,799,151; and 4,347,837. A previously-proposed endoscope that had a provision to control the degree of bending is described in U.S. Pat. No. 3,557,780.

The steering mechanisms for these previously-proposed endoscopes are rather elaborate structures, with many parts that can fail and which are relatively expensive to produce. Further, in many cases it has been necessary to provide the cables with a significant amount of slack or play because the steering sections bend at discrete points, and not in a perfectly smooth curve.

U.S. Pat. No. 4,700,693, Oct. 23, 1987, and having a common assignee herewith, addresses the above problem. The disclosure in that patent is incorporated herein by reference.

In the steering section of the endoscope or borescope described in U.S. Pat. No. 4,700,693, the steering section has, within its flexible sheath, a plurality of axially aligned washers, each having a central passage and a number of peripheral bores. Pairs of these peripheral bores are disposed generally diametrically opposite each other. The steering cables pass through the respective axially aligned peripheral bores of the washers, and spacing structure is disposed at the location of predetermined ones of these peripheral bores to define bending locations for the steering section, such that the displacement of certain pairs of the steering cables results in bending of the steering section in one plane or another. As disclosed in that patent application, the washers are flat washers, and the spacer structure includes pairs of hemispherical beads that are disposed in nose-to-nose fashion over the respective cables between successive washers. The beads have their spherical surfaces facing one another, and their flat surfaces facing outward against their associated washers.

The upshot of this construction is that when the steering section is bent, the spherical surfaces of the hemispherical beads should roll over one another to achieve smooth bending without a significant amount of slack or play in the cable.

Unfortunately, with this design, the hemispherical spacer beads tended to degrade in service over time. The basic reason for this is that the steering cable had to have a significantly smaller diameter than the diameter of the through-bore of the beads to achieve proper clearance for the cable. Because of the difference in diameters of the cable and the spacer bead through-bores, there is a tendency for the hemispherical spacer beads to shift off axis by the amount of the clearance. When the spacer beads rock over one another, the intersecting edges of the through-holes cut into one another in the radially displaced beads. This eventually works into a saddle and binds on the cable.

In order to avoid this problem, it was necessary to provide a relatively wide bearing surface at the facing noses of the beads to compensate for this lateral sliding of the spacers relative to one another. However, if the nose surface is wide enough to compensate for the entire clearance between the steering cable and the spacer bead through-bores, then as one spacer bead tilts with respect to another, the effective track length of the cable is increased. Since the actual cable length does not increase, the effect of this is to tighten the cable when the steering section is deflected, and thereby increase steering forces.

Of course, a smaller bearing nose surface could be employed if there were a smaller diametrical clearance between the cable and spacer bead, but in that case the cable would bind against the spacer beads when the spacers tilted with respect to each other.

A further approach to this problem is to employ pairs of tapered spacer beads that have a relatively wide base surface facing the associated washer and a relatively flat nose surface facing against the like nose surface of the other spacer bead. The beads each have an axial bore that is flared out towards the base, so that the bead has a small clearance over the steering cable at the nose surface, but a wide clearance at the base to prevent the spacer beads from binding on the cable.

This configuration, while an improvement over previous designs, does still have some tendency to bind on the cable. One reason for this is that the dual spacer beads will make two points of contact with the cable, that is, at the narrow nose portion of each bead. Also, the rocking motion of the conic beads on one another does produce a noticeable tightening of the control cable, although certainly a smaller amount of tightness than would be encountered with previous designs.

Still further, it is somewhat difficult to string the beads onto the cable when the endoscope steering section is being assembled, because for one of each pair of beads the cable must be threaded into the narrow nose portion of the through-bore.

OBJECTS AND SUMMARY OF THE INVENTION

Accordingly, it is an object of this invention to provide an endoscope or borescope bendable steering section that avoids the drawbacks encountered with previously proposed designs.

It is a further object of this invention to provide a steering section which keeps the slack or play in the steering cables to a minimum, but which will not bind the steering cables when bent.

It is a still further object of this invention to provide a bendable steering section with smooth, crisp, responsive, and precise bending action.

As aforesaid, this invention resides in the steerable endoscope or borescope of the type having a viewing head and a cable-bendable steering section disposed proximally of the viewing head. The steering section has a flexible sheath, a plurality of washers, with each of the washers having a central passage and a plurality of peripheral bores therethrough, a plurality of steering cables passing through respective axially aligned ones of the peripheral bores of the washers, and pairs of spacer beads disposed between certain successive washers over the steering cables such that the beads can roll or slide with respect to each other to define the bending locations for the endoscope.

According to an aspect of this invention, the pairs of beads each include one convex, round-nosed "ball" bead and one concave-faced "socket" bead, with the ball bead slidably contacting the mating concave face of the socket bead. The socket bead can have a relatively wide bore relative to the cable diameter, in a preferred embodiment on the order of three times the cable diameter, so that the socket bead, despite any sliding against the associated washer, stays out of contact with the cable. The ball bead preferably has a tapered axial bore that flares out in the direction towards the associated washer. Consequently, the ball bead makes contact with the cable only at a single point, i.e., towards the nose of the ball bead. The peripheral bores of the washer are also flared out from a medial waist portion so that the cable contacts the washer only at the waist portion. As a result, even though there is much less slack or play in the cable, the endoscope steering section remains easy to work, even when fully deflected.

In certain preferred embodiments, spacer limiter beads are disposed over the cables in the spaces between washers that alternate with the ball and socket bead locations. These limiter beads have an axial thickness half the axial distance between washers. This limits the amount of bending for a portion of the endoscope steering section so that the principal bending will occur at a desired location. Preferably, these limiter beads are also flared out both fore and aft from a medial waist portion so as to contact the cable only at a single location.

The above and many other objects, features, and advantages of this invention will be more fully understood and appreciated from the following detailed description of a preferred embodiment, which should be considered in connection with the accompanying drawing.

DETAILED DESCRIPTION OF THE PREFERRED EMBODIMENTS

Figure 1:
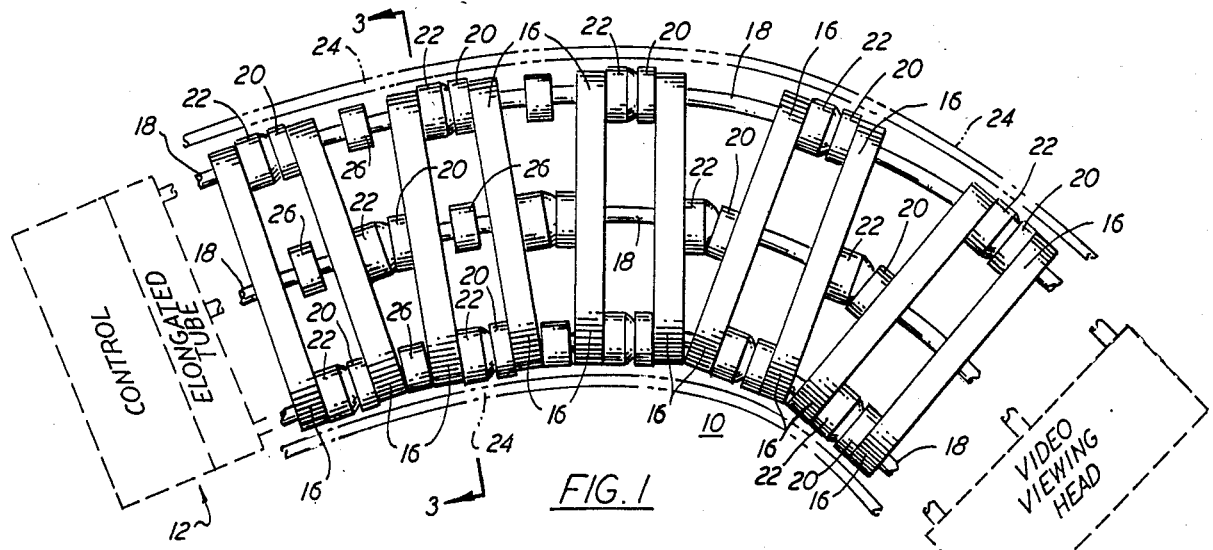
FIG. 1 is a schematic view of a steering section of an endoscope or borescope according to a first embodiment of this invention.
Figure 2:
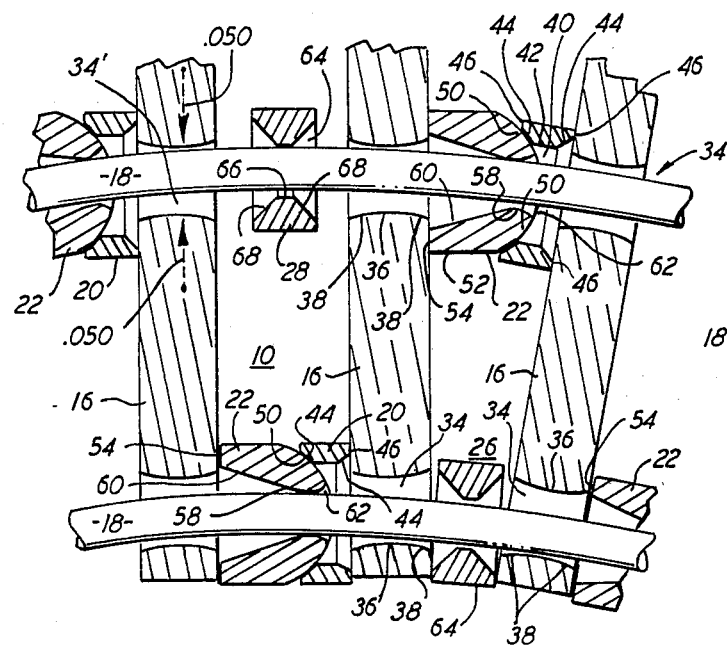
FIG. 2 is a detailed sectional view of a portion of the sleeving section of FIG. 1, and then at line 2—2 of FIG. 3.

Referring now to the drawing, and initially to FIGS. 1 and 2 thereof, a generally cylindrical steering section 10 of one type of endoscope has its proximal end (to the left in the drawing) connected by means of an elongated flexible tube to a control section 12, and on its distal end (to the right in the drawing) is mounted a video or fiber optics type viewing head. The steering section 10 is formed of a stack of washers 16, a typical one of which is shown in plan in FIG. 3. With these washers there are associated two pairs of steering cables 18, which are preferably twisted strand stainless steel cables. The paired socket spacer beads 20 and ball spacer beads 22, shown in section in FIGS. 4 and 5, respectively, are disposed over the cables 18 in the alternate spaces between successive washers 16, i.e. at alternate pairs of the steering cables 18, considered in progression from one washer to the next. The assembly is covered with a flexible sheath 24.

Figure 6:
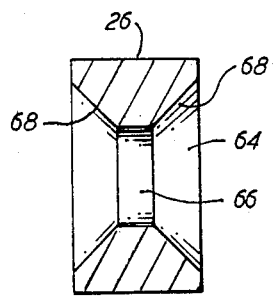
FIG. 6 is a sectional view of a limiter spacer bead as employed in this embodiment.

Spacer limiter beads 26 are strung onto the cables 18 at selected locations, i.e., in several of the interwasher spaces not occupied by the ball and socket beads 22, 20. These typically have an axial thickness about one-half the spacing between washers 16, as defined by the pair of beads 20 and 22, and serve to limit the amount of bending at the selected locations. Preferably, these spacer limiter beads 26 are located at the first four interwasher spaces considered from the proximal end of the steering section 10. A cross section of the spacer limiter bead 26 is shown in FIG. 6.

Figure 3:
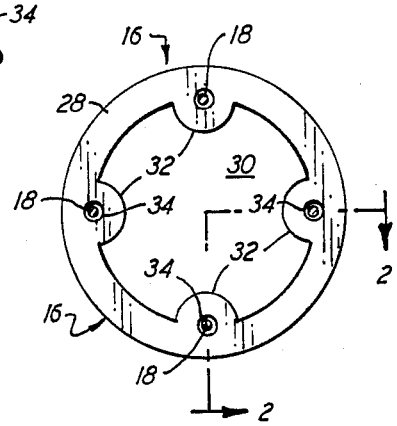
FIG. 3 is a plan view showing a washer of the first embodiment at line 3—3 of FIG. 1.

The washers 16 as shown in FIG. 3 can favorably be composed of aluminum bronze or beryllium copper. The washers 16 are basically in the form of a circular ring 28 which has a generally cruciform central passage 30 defined among four inwardly directed lobes 32 that are spaced at ninety-degree intervals on the ring 28. Peripheral through-bores 34 penetrate these lobes 32, and the steering cables 18 pass through these bores 34. The stack of washers 16 has respective bores 34 aligned in registry with one another.

As shown in FIG. 2, the through bores 34 are flared out axially, both fore and aft. That is, each through bore 34 has a medial generally cylindrical waist portion 36, extending over about the middle third of the bore 34, and flared or frustoconic portions 38 which open out toward the surfaces of the washer 16. The waist portion diameter is about one-and-one-half times the cable diameter, and the end diameter of the flared portions 38 is about twice the cable diameter. This structure ensures that where the steering section 10 is bent, the cable 18 will touch the washers 16 only at a single point, namely at the waist portion 36 of the bore 34. This permits cable slack or play to be substantially eliminated, resulting in superior control of the bending of the steering section 10, especially in the delicate body cavities of a patient. Also, this structure results in much smoother, relatively effortless operation of the cables 18, even when the steering section 10 is already sharply deflected in one plane or the other.

As indicated at the left side of FIG. 2, the washer 16 can alternatively be provided with a bore 34' having a smoothly curved internal surface. In this case the bore 34' is of generally toroidal shape with a radius of curvature of 0.050 inches. Here, the cable 18 makes rolling contact with the surface of the bore 34' as the endoscope steering section is bent.

In this embodiment the endoscope is in the form of a colonoscope, having a nominal diameter of 13.5 millimeters. The diameter of the cable 18 is substantially 0.027 inches and the diameter of the narrow waist portion 36 of the through bore 34 is substantially 0.032 inches to 0.034 inches.

Figures 4, 5:
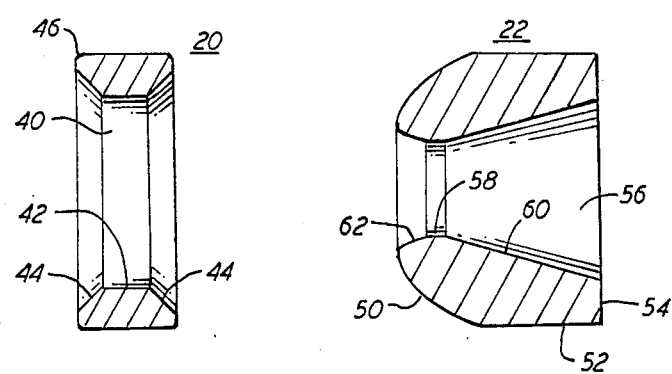
FIG. 4 is a sectional view of a socket type bead as employed in this first embodiment.
FIG. 5 is a sectional view of a ball type bead as employed in this embodiment.

Referring to FIG. 4, the socket beads 20 each are in the form of a ring with an axial thickness of 0.031 inches and an outer diameter of 0.088 inches. The socket beads 20 have a flared or countersunk through-passage 40 that has a central, generally cylindrical portion with a diameter of about 0.062 inches and flared out portions 44 to either side that expand to a diameter of 0.078 inches at the faces of the beads 20. This leaves a relatively narrow rim 46 that is in sliding contact with the lobe 32 of the associated washer 16. The countersunk portions 44 of the socket bead through-passages 40 have an included angle of about ninety degrees. These beads 20 are axially symmetrical, and can be strung onto the cables 18 in either orientation. Because the through-passages 40 are about three times the cable diameter, it is a simple matter to thread the socket beads 20 onto the cables 18.

Turning now to FIG. 5, the ball bead 22 is shown to have a generally spherical nose surface 50, here with a radius of 0.0465 inches, that is joined by a cylindrical portion 52, of 0.088 inches diameter, to a flat base portion 54 that is in sliding contact with the lobe 32 of the associated washer 16. The bead 22 has central axial through-passage 56 with a narrow waist portion 58, here of 0.032 inches diameter, and flared out portions 50 and 62 directed respectively towards the base 54 and the nose of the bead 22. These flared out portions 60 and 62 each have an included angle of thirty degrees. The portion 60 has an opening diameter of 0.059 inches. The waist portion 58 is situated about 0.009 inches from the nose opening of the portion 62, i.e., from the nose end of the bead 22.

Referring now to FIG. 6, the spacer limiter beads 26 of this embodiment have an axial thickness of about 0.042 inches and a diameter of about 0.075 inches. The beads 26 have an axial through-passage 64 that is countersunk at both ends, with a medial waist portion 66 of 0.032 inches diameter, and flared out or countersunk portions 68 both fore and aft which expand to opening diameters of 0.062 inches. These portions 68 have included angles of ninety degrees.

The ball and socket beads 22,20 fit together, as best shown in FIG. 2, with the spherical nose surface 50 of the ball bead in sliding contact with the facing countersunk portion 44 of the socket bead 20 with which it is paired. The two beads 20 and 22 together define a washer spacing between successive washers, here about 0.085 inches, and the pairs of beads 20,22 define bending points for the endoscope steering section 10. The control cables 18 contact each such pair of ball and socket beads 20,22 at most at a single point, namely at the narrow waist portion 58 of the ball bead 22.

The limiter beads 26, which are here half the axial thickness of the interwasher spaces, limit the amount of bending to half the angle which would be obtained at that bending location if the bead 26 were not present. In other words, if no spacer limiter bead is situated at a bending location, the washers will continue to tilt relative to each other until there is contact between them. The spacer limiter beads 26 are preferably employed at several interwasher spaces towards the proximal end of the steering section 10. The nature of a cable-and-washer type steering section is to bend first at the proximal end and then more and more distally as the control cables 18 are displaced. Situating these beads 26 proximally concentrates the sharper bending towards the distal end i.e., towards the viewing head 14.

Because of the flared nature of the through-bores 34 and through-passages 40, 56, and 64, as well as the size of the through-passages 40, it is relatively simple to string the control cables 18 thorugh the washers 16 and to string the beads 20, 22, and 26 onto the control cables. This is highly significant where the assembly of the steering section 10 is carried out by hand, and it simplifies the machine tolerances required where the assembly is automated.

As aforementioned, the double-tapered nature of the passages and bores of the beads 20, 22, 26 and washers 16, in concert with the ball-and-socket action of the beads 20 and 22, substantially eliminates play or slack in the control cables 18, and reduces cable friction as well. Consequently, steering drag is substantially eliminated even where the steering section is to be bent in one axis when already fully deflected in another axis. The control cables 18 are not stretched out over time, and the endoscope steering section life cycle is greatly lengthened.

The beads 20, 22, and 26 can be formed of a suitable metal such as Beryllium copper. The beads 20, 22 and 26 can also be provided with curved through passages, akin to the curved bore 34', instead of the countersunk, flared out, or conic passages illustrated here.

While the foregoing describes a single preferred embodiment, it should be clear that many modifications and variations thereof would be possible, and would present themselves to those of skill in the art without departure from the scope and spirit of this invention, as defined in the appended claims.

We claim:

1. In a steerable endoscope or borescope of the type having a viewing head, a cable-bendable steering section proximally of the viewing head and including a flexible sheath, a plurality of axially aligned generally flat washers each having a central passage and a plurality of peripheral bores therethrough pairs of which are generally diametrically disposed, a plurality of steering cables passing through respective axially aligned peripheral bores of said washers, and pairs of spacer beads disposed at the locations of at least certain ones of said steering cables and serving to define bending locations for said steering section such that displacement of one opposed pair of the steering cables results in bending of the steering section; the improvement wherein said pairs of spacer beads include a ball bead and a socket bead, respectively having a convex surface and a concave surface in sliding contact relative to one another, and each having a relatively flat surface disposed against an associated one of said washers.

2. The steerable endoscope of claim 1 wherein said socket bead has an axial through passage that is on the order of three times the cable diameter, so that said socket bead remains out of contact with the associated steering cable.

3. The steerable endoscope of claim 1 in which said ball bead has a tapered axial through passage that is flared in the direction towards the associated washer.

4. The steerable endoscope of claim 1 wherein each said pair of beads touches the associated control cable at a single point.

5. The steerable endoscope of claim 1 wherein for each said control cable said pairs of spacer beads are disposed in alternate spaces between said washers, and together define a predetermined spacing between said successive washers; and further comprising limiter beads slidably disposed on said control cables in at least certain ones of the remaining spaces to limit the bending of the steering section.

6. The steerable endoscope of claim 5 wherein said limiter beads have an axial thickness substantially one-half the predetermined spacing between successive washers.

7. The steerable endoscope of claim 6 wherein said limiter beads have an axial through-passage that is flared out from a medial portion thereof towards both of the associated washers.

8. The steerable endoscope of claim 1 wherein said peripheral bores of the washers are flared out both axially fore and aft from a medial waist portion, so that the associated cable passing therethrough contacts the washer only at said waist portion.

9. The steerable endoscope of claim 8 wherein said waist portion has a diameter on the order of one and one-half times the diameter of the steering cable.

10. In a steerable endoscope or borescope of the type having a viewing head, a cable-bendable steering section proximally of the viewing head and including a flexible sheath, a plurality of axially aligned generally flat washers each having a central passage and a plurality of peripheral bores therethrough pairs of which are generally diametrically disposed, a plurality of steering cables passing through respective axially aligned peripheral bores of said washers, and pairs of spacer beads disposed at the locations of at least certain ones of said steering cables and serving to define bending locations for said steering section such that displacement of one opposed pair of the steering cables results in bending of the steering section; and wherein for each said control cable said pairs of beads are disposed in alternate spaces between successive washers and together define a predetermined spacing between said successive washers; the improvement wherein limiter beads are slidably disposed on said control cables in at least certain ones of the remaining spaces to limit the bending of the steering section.

11. The steerable endoscope of claim 10, wherein said limiter beads have an axial thickness substantially one-half the predetermined spacing between successive washers.

12. The steerable endoscope of claim 10, wherein said limiter beads have an axial through passage that is flared out from a medial portion thereof towards both of the associated washers.

13. The steerable endoscope of claim 10 wherein said peripheral bores of the washers are flared out both axially fore and aft from a medial waist portion that has a diameter on the order of about one and one-half times the steering cable diameter.

14. The steerable endoscope of claim 12 in which the flared axial through passages of the limiter beads have an included angle of substantially ninety degrees.

15. In a steerable endoscope or borescope of the type having a viewing head, a cable-bendable steering section proximally of the viewing head and including a flexible sheath, a plurality of axially aligned generally flat washers each having a central passage and a plurality of peripheral bores therethrough pairs of which are generally diametrically disposed, a plurality of steering cables passing through respective axially aligned peripheral bores of said washers, and pairs of spacer beads disposed at the locations of at least certain ones of said steering cables and serving to define bending locations for said steering section such that displacement of one opposed pair of the steering cables results in bending of the steering section; the improvement wherein the peripheral bores of the washers are flared out both axially fore and aft from a medial waist portion, so that the associated cable passing therethrough contacts the washer only at said waist portion.

16. The steerable endoscope of claim 15 wherein said medial waist portion is generally cylindrical and said bore has fore and aft frustoconic portions extending from the waist portion to outer surfaces of the washer.

17. The steerable endoscope of claim 15 wherein said bore is smoothly curved such that the control cable makes rolling contact therewith as said steering section is bent.

18. The steerable endoscope of claim 17 wherein said bore is substantially toroidal.

* * * * *